United States Patent [19]

Kuriyama et al.

[11] Patent Number: 4,865,445

[45] Date of Patent: Sep. 12, 1989

[54] APPARATUS FOR DETECTING FAULTS ON THE SURFACE OF A RESIST MASTER DISC AND MEASURING THE THICKNESS OF THE RESIST COATING LAYER

[75] Inventors: Kazumi Kuriyama; Shigeru Kono; Yutaka Takasu; Chiharu Koshio; Kazuhiko Nagata, all of Yamansahi, Japan

[73] Assignee: Pioneer Electronic Corporation, Tokyo, Japan

[21] Appl. No.: 94,777

[22] Filed: Sep. 10, 1987

[30] Foreign Application Priority Data

Sep. 10, 1986 [JP] Japan .................................. 61-213345

[51] Int. Cl.$^4$ ...................... G01B 11/06; G01N 21/89
[52] U.S. Cl. .................................... 356/73; 356/237; 356/382
[58] Field of Search ................. 356/73, 445, 381, 382, 356/429, 430, 431, 237

[56] References Cited

U.S. PATENT DOCUMENTS

| | | | |
|---|---|---|---|
| 3,492,491 | 1/1970 | Beeh | 356/381 |
| 3,841,761 | 10/1974 | Selgin | 356/430 |
| 4,310,250 | 1/1982 | Sick et al. | 356/431 |
| 4,391,524 | 7/1983 | Steigmeier et al. | 356/338 |
| 4,454,001 | 6/1984 | Sternheim et al. | 356/382 |
| 4,676,646 | 6/1987 | Strand et al. | 356/381 |
| 4,676,883 | 6/1987 | Nelson et al. | 356/382 |

FOREIGN PATENT DOCUMENTS

| | | | |
|---|---|---|---|
| 179648 | 11/1982 | Japan | 356/445 |
| 55705 | 4/1983 | Japan | 356/381 |

Primary Examiner—Richard A. Rosenberger
Attorney, Agent, or Firm—Foley & Lardner, Schwartz, Jeffery, Schwaab, Mack, Blumenthal & Evans

[57] ABSTRACT

An apparatus for detecting faults on the surface of a resist master disc and for measuring the thickness of the resist coating layer includes a single light source for generating a laser beam for inspection of the master disc, a first separator for separating the laser beam into a first laser beam which is used for the detection of faults, and a second laser beam which is used to measure the thickness of the resist coating layer. The second laser beam is further separated into two laser beams one of which is irradiated on the surface of the resist coated master disc at a given angle of incidence. The detection of faults on the surface of the master disc is performed by detecting a level change of the quantity of reflection light of the first laser beam from the resist master disc, and the measurement of the thickness of the resist layer is performed by using a ratio between quantities of two laser beams obtained from the second laser beam one of which is detected after being reflected by the surface of the resist master disc.

4 Claims, 3 Drawing Sheets

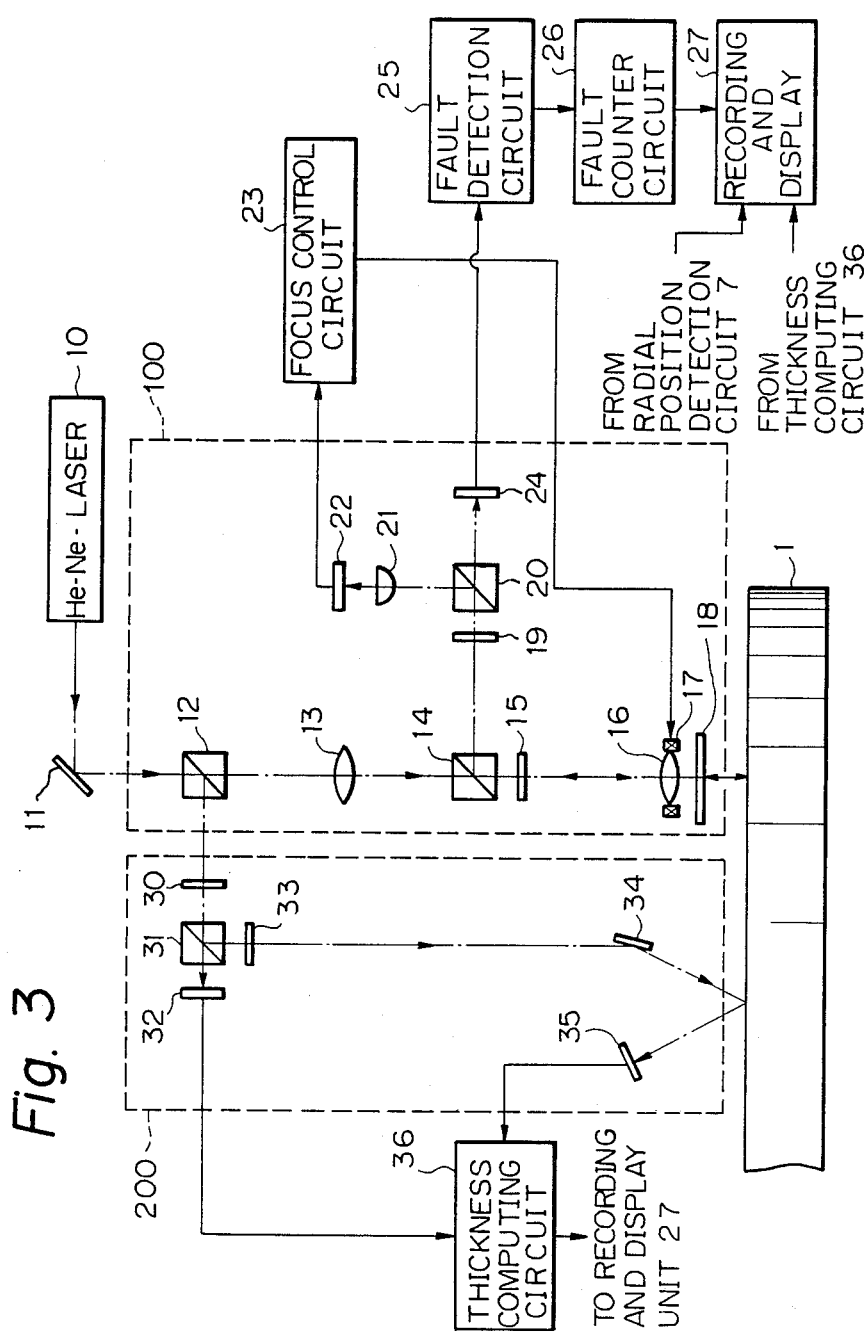

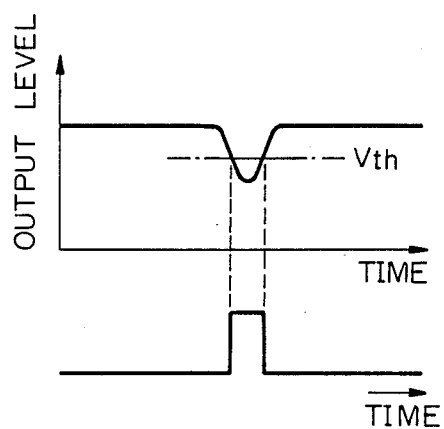
Fig. 4A
Fig. 4B
Fig. 5
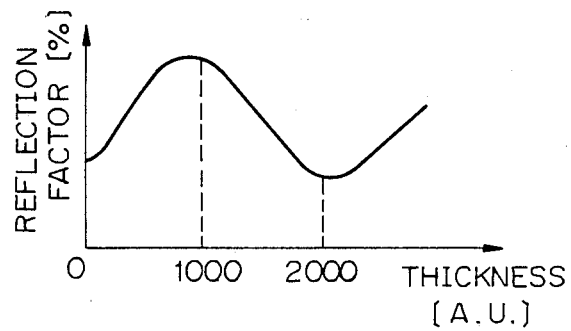

APPARATUS FOR DETECTING FAULTS ON THE SURFACE OF A RESIST MASTER DISC AND MEASURING THE THICKNESS OF THE RESIST COATING LAYER

BACKGROUND OF THE INVENTION

1. Field of the Invention

The present invention relates to an apparatus for detecting faults on the surface of a resist master disc for producing optical discs and measuring the thickness of the resist coating layer on the master disc.

2. Description of Background Information

The optical recording of information is in practical use as a method in which video and audio information is recorded on a disc shaped recording medium.

In one typical process of producing an optical information recording disc, a resist master disc is prepared by coating a glass disc used as a substrate with a thin layer of a resist material. The master disc is treated in the so called bit by bit system exposure process in which the resist layer is exposed to a finely focused laser beam which is modulated in a blinking manner with the video and audio information to be recorded. Subsequently, the master disc is treated by a development process in which exposed portions of the resist thin layer are removed to form a series of pits which carry the information to be recorded in the form of the length of each pit and its repetition rate.

In optical information recording using optical discs, loss of recorded information generally called as a "drop out," is rather difficult to eliminate. Therefore it is necessary, in the process of producing the master disc, to detect the presence of faults such as dust, defects, or flaws on the surface of the master disc which may cause a drop out. On the other hand, it is also very important that the thickness of the thin resist coating layer on the surface of the glass master disc be maintained constant. Therefore, it is equally necessary to measure the thickness of the resist layer.

Conventionally, for detecting faults on the surface of the master disc and for measuring the thickness of the resist layer, an apparatus for detecting faults on the surface of a resist master disc and an apparatus for measuring the thickness were prepared separately. An example of conventional measuring process is as follows. When the detection of faults by the first apparatus is completed, the master disc is transported, by hand, to the thickness measuring apparatus where the thickness of the resist layer is measured.

Therefore, an increase of the cost was not avoided because of the necessity for preparing two apparatuses, and a long time was required for completing both of the detection of faults and the measurement of the thickness.

SUMMARY OF THE INVENTION

An object of the present invention is, therefore, to eliminate the above mentioned deficiencies of the conventional technique, and to provide an apparatus for detecting faults on the surface of a master disc and for measuring the thickness of the resist coating layer, which is capable of reducing the cost and reducing the time for detecting faults and measuring the thickness by combining two units having the function of detecting flaws and the function of measuring the thickness of resist coating layer respectively, into a single apparatus having both functions.

According to the present invention, an apparatus for detecting faults on the surface of a master disc and for measuring the thickness of the resist coating layer includes a first optical system for detecting faults and a second optical system for measuring the thickness of the resist coating layer, and a light source for both of optical systems, and constructed to allow a parallel processing of the detection of faults and the measurement of thickness.

BRIEF DESCRIPTION OF THE DRAWINGS

FIG. 3 is a schematic diagram showing an example of structure of an optical unit and peripheral circuits used in the construction shown in FIG. 1;

FIGS. 4A and 4B are waveform diagrams respectively showing an output signal of a PIN photo diode 24 and a detection output pulse of a fault detection circuit 25 respectively, of the optical unit shown in FIG. 3; and FIG. 5 is a diagram showing the relationship between the reflection factor of the surface of the master disc and the thickness of the resist coating layer.

DETAILED DESCRIPTION OF THE PREFERRED EMBODIMENT

Figure 1:
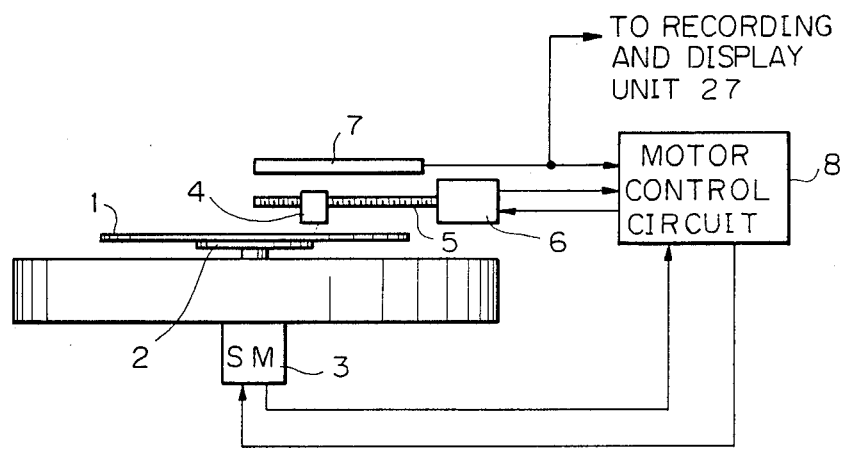
FIG. 1 is a schematic diagram showing the construction of an apparatus for detecting faults on the surface of a master disc and for measuring the thickness of resist coating layer.

Reference is first made to FIG. 1 showing the construction of an apparatus for detecting faults on the surface of master disc and for measuring the thickness of the resist coating layer.

As shown, a resist coated master disc 1 is mounted on a turntable 2 which is rotated by a spindle motor 3. At a position above the resist coated master disc 1, there is provided an optical unit 4 for optically detecting faults on the surface of the resist coated master disc and for optically measuring the thickness of the resist coating. For the purpose of illustration, the optical unit 4 is shown as a small box in FIG. 1. However, it should be noted that the optical unit 4 includes various elements which will be described with reference to FIG. 3. The optical unit 4 is mechanically engaged, by means of a known element which is not illustated in this figure, with a screw gear shaft 5 which lies transversely along a radial axis of the resist coated master disc 1. The screw gear shaft 5 is rotated by a feeding motor 6, and the optical unit 4 is moved linerly in a direction determined by the direction of rotation of the screw gear shaft 5. The position of the optical unit through the movement along the radial axis is detected by means of a radial position detection circuit 7 which supplies information indicating the position of the optical unit 4, especially, the position of the laser beam irradiated on the surface of the resist master disc 1, along the radial direction of the disc, to a motor control circuit 8. As the radial position detection circuit 7, any of known devices such as a variable resistor which is arranged so that its resistance value is varied as the movement of the optical unit can be used. The motor control circuit 8 is operative to control the rotational speed and the direction of the feed motor 6 in order to control the position of the optical unit 4, and to control the rotational speed of the spindle motor 3 in accordance with the information from the radial position detector 7, according to a CLV (constant linear velocity) system, so that the linear velocity of the resist coated master disc 1 at each radial position to which the optical unit 4 is moved is made constant.

Figure 2:
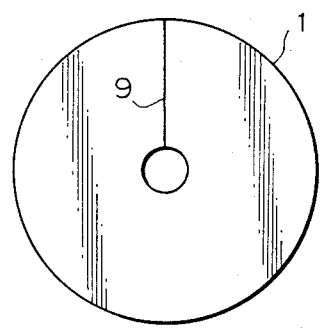
FIG. 2 is a view schematically showing a master disc having a flaw on its surface.

The reason of utilizing the CLV system for driving the spindle motor 3 is discussed as follows. That is, as shown in FIG. 2, if a scratch 9 having a uniform width t (millimeters) is present on the surface of the resist coated master disc 1 from an inner part to an outer periphery along a radial direction of the resist coated master disc 1, the pulse width W of a detection pulse obtained by the optical unit 4 is expressed by the following equation:

$$W = t/2\pi R \cdot f \text{ (seconds)}$$

where f represents the rotational speed of the resist coated master disc 1, and R represents the radius of detection (the radius of the resist coated master disc 1 at which the optical unit 4 is located). Therefore, if the rotational speed f of the resist coated master disc is constant, the pulse width W of the detected pulse will be changed depending on the radius R of detection. In order to utilize this pulse width as a standard of the magnitude of a fault through the inspection, it is necessary that the pulse width W becomes unchanged if the width t of a fault is constant. Therefore, the inspection must be carried out while maintaining the linear velocity V ($V = 2\pi R \cdot f$) constant. The use of CLV system means that the rotational speed f of the resist coated master disc satisfies the following equation: ps
$$f = K/R$$

where K is a certain constant.

As a result of the above control procedure, the pulse width W will be expressed by the following equation:

$$W = t/2\pi K$$

Thus, the pulse width W of the detection pulse becomes proportional to the width t of the scratch irrespectively of the radius R of the inspection position.

Referring to FIG. 3, the description is further made as to the construction of the optical unit 4 which optically detects faults on the surface of the resist coated master disc 1 and measures the thickness of the resist coating layer.

As shown, the apparatus includes an He-Ne (helium-neon) laser tube 10 as a single light source. A laser beam generated by this He-Ne laser 10 is directed to a beam splitter 12 by which the laser beam generated by the He-Ne laser is separated into a first laser beam for the detection of faults and a second laser beam for the measurement of the thickness of the resist coating layer.

The first laser beam for the detection of faults passes straight through a diversing lens 13, a beam splitter 14 and a λ/4 plate 15 and directed into an objective lens 16. By the objective lens 16, the first laser beam is converged into a minute light spot impinging perpendicularly upon the surface of the resist coated master disc 1. The objective lens 16 is driven in the direction of the optical axis thereof by means of a focus actuator 17. In order to prevent the surface of the resist coated master disc 1 from being stained by dust formed by the frictional movement of the focus actuator 17, a glass plate 18 is provided between the objective lens 16 and the resist coated master disc 1. The first laser beam is then reflected by the surface of the resist coated master disc 1 and passes straight through the glass plate 18, the objective lens 16 and the λ/4 plate 15 and applied to the beam splitter 14. At the beam splitter 14, the first laser beam from the resist coated master disc 1 is reflected at a right angle with respect to the incident beam and orientated to a λ/2 plate 19 and a beam splitter 20. At the beam splitter 20, the reflection beam of the first laser beam is further separated into two laser beams for detecting the focus error and for detecting faults respectively. The laser beam for detecting the focus error is directed to a quadrant light detector 22 whose light receiving surface is divided into four segments, after passing through a cylindrical lens 21. The quadrant light detector 22 generates four output signals whose levels respectively represent the quantity of light received by each segment of the light detector 22. The output signals of the light detector 22 are supplied to a focus control circuit 23 which generates a focus error signal in accordance with the output signals of the light detector 22, and generates a control signal for controlling the position of the objective lens 16 with respect to the resist coated master disc 1 so that the level of the focus error signal is maintained always constant, e.g., at a value of zero. The method utilized in this embodiment for generating the focus error signal is the so called astigmatism method which is well known in the field of optical disc player systems. The laser beam for the detection of faults which passed through the beam splitter 20 enters a light detection element 24 such as a PIN photo diode at which an electric output signal representing the quantity of incident light is generated. The output signal of the PIN photo diode 24 is supplied to a fault detection circuit 25. If there is a fault such as a flaw on the surface of the resist coated master disc 1, a signal level of the output signal of the PIN photo diode 24 will drop partially as illustrated in FIG. 4A. Therefore, by setting a predetermined threshold level in the fault detection circuit 25, a fault detection pulse signal as illustrated in FIG. 4B can be obtained. For example, the fault detection circuit 25 may include a comparator which receives the output signal of the PIN photo diode 24 and the threshold level and adapted to produce an output signal when the level of the output signal of the PIN photo diode 24 becomes lower than the threshold level. This fault detection pulse signal is in turn supplied to a fault counting circuit 26. Since the pulse width of the fault detection pulse signal corresponds to the width t of the fault part as mentioned before, the width t of the fault part can be distinguished by means of the pulse width of the fault detection pulse signal. Therefore, the fault counting circuit 26 is constructed to have a plurality of windows corresponding to different pulse widths, so as to count the number of fault parts for each of the pulse width. The distinction of the pulse width of the fault detection pulse signal can be performed by any known method. For example, a predetermined clock signal is counted during the presence of the fault detection pulse signal, so that the count value represents the duration of the pulse signal. Also, the pulse width of the fault detection pulse signal can be determined after converting the pulse width into a voltage signal. Count values obtained at the fault counting circuit 26 are preferably supplied to a recording and display unit 27 which also receives the output signal of the radial position detection circuit 7 and a thickness computing circuit 36, described later. The recording and display unit 27 is, for example, constructed to have a printer and a LED display panel. The count values of the number of faults and the thickness values are printed out and displayed on the LED display panel. It is to be noted that the recording and display unit 27 can be replaced by a unit having only one of recording and displaying functions. Furthermore, the recording and display unit 27 can be omitted if the count signals of the number of fault parts and the signal indicative of the thickness of the resist layer are directly supplied to any external apparatus. By the elements described above, a fault detection optical system 100 for optically detecting faults on the surface of the resist coated master disc 1 is constituted.

In the above described embodiment, the counting of the number of faults is effected for each of the size of the fault. However, it is preferable to arrange the apparatus so as to memorize the radial position of the detected fault in a memory device provided in the recording and display unit 27 in relation to the position detection information from the radial position detection circuit 7 shown in FIG. 1.

The explanation is further made to a thickness detecting optical system 200 for measuring the thickness of the resist coating layer. The laser beam for the measurement of the thickness separated by the beam splitter 12 is directed to a λ/2 plate 30 and another beam splitter 31. At the beam splitter 31, the laser beam is separated into two light beams one of which is applied directly to a photo detector 32 which generates an electric output signal according to the quantity of incident light. The other one of the separated laser beams passes through a λ/2 plate 33 and directed to a mirror 34. At the mirror 34, the laser beam is orientated to the surface of the resist coated master disc 1. By the mirror 34, the laser beam is irradiated on the surface of the resist coated master disc 1 at a given angle of incidence. It is to be noted that in this arrangement that the laser beam is irradiated on the surface of the resist coated master disc 1 without passing through any lens, i.e., in the form of a plane wave. The laser beam irradiated on the surface of the resist coated master disc 1 and reflected thereby then enters a photo detector 35 which is located at a position suited receiving the reflected laser beam and which generates an electric signal representing the quantity of incident light. The output signals of the photo detectors 32 and 35 are supplied to the thickness computing circuit 36. In the thickness computing circuit 36, the output signal of the photo detector 35 is divided by the output signal of the photo detector 32, to generate a rate between the quantities of light received by the photo detectors 35 and 32.

In the case of the resist coated master disc to be treated by this embodiment of the present invention, there is such a relationship as indicated by a curve in FIG. 5 between the reflection factor P and the thickness of the resist coating layer. More specifically, within a range of the thickness from 1000 to 2000 A.U. (angstrom unit), there is an inversely proportional relation between the reflection factor and the thickness of the resist coating layer. Therefore, by calculating the reflection factor by using the output signals of the photo detectors 32 and 35, the thickness h can be measured within the range from 1000 to 2000 A.U. Moreover, since the thickness of the resist coating layer of the resist coated master disc 1 is usually within the above range, the range from 1000 to 2000 A.U. is practically sufficient for the measurement of thickness h of the resist coating layer. In addition, it is also possible to vary the range of the measurement of thickness by changing the wavelength of the laser beam from the light source (by replacing the He-Ne laser 10 with any other laser source).

The thickness value detected by this thickness computing circuit 36 is in turn supplied to the recording and display unit 27 as mentioned before. In this measurement of the thickness of coating, it is possible to design the apparatus so that the radial position at which the thickness varies largely is memorized in the memory device in the recording and display unit 27, as in the detection of faults described before.

In this connection, it is to be noted that the radial position of the resist coated master disc 1 at which the laser beam reflected by the mirror 34 is irradiated can be also determined by means of the output signal of the radial position detection circuit 7. This is because the distance on the surface of the resist coated master disc 1 between the position at which the laser beam is irradiated by the objective lens 16 and the position at which the laser beam reflected by the mirror 34 is irradiated is constant. Therefore, the radial position of the irradiation of the laser beam reflected by the mirror 34 can be calculated by subtracting the distance between two laser beams from the radial position detected by the radial position detection circuit 7. Such a function of calculation can be provided in the recording and display circuit 27.

In the above described embodiment, the detection of faults and the measurement of the thickness of the resist coating layer are performed at the same time. However, the application of the apparatus according to the present invention is not limited to this, and the apparatus can be used in the case of detection of faults on a glass master disc without the resist coating layer before coating the master disc with the resist material. In this case, since the master disc is not coated with the resist material, only detection of faults is executed by the apparatus according to the present invention in that case.

It will be appreciated from the foregoing, the apparatus for detecting faults on the surface of a master disc and for measuring the thickness of the resist coating layer according to the present invention includes an optical system for detecting faults, an optical system for measuring the thickness of the resist coating layer, and a common light source so that the detection of faults and the measurement of the thickness can be performed at the same time. Therefore, the size and the cost of the apparatus are greatly reduced by combining functions for detecting faults and for measuring the thickness which were conventionally presented independently. Moreover, the apparatus according to the present invention is advantageous in that the time period required for the inspection i.e., the detection of faults, and the measurement is significantly shortened.

What is claimed is:
1. An apparatus for the detection of faults on the surface of a resist master disc and for the measurement of the thickness of a resist layer coating said resist master disc, comprising:
   a single light source;
   first separating means for separating a light beam generated by said source of light into a first light beam and a second light beam;
   first irradiation means for irradiating said first light beam on the surface of said resist master disc in the form of a minute beam spot;

fault detection means for detecting faults on said surface of said resist master disc by using reflected light of said first light beam from said resist master disc;

second separating means for separating said second light beam into a third light beam and a fourth light beam;

second irradiating means for irradiating said third light beam on said surface of said resist master disc at a given angle of incidence;

thickness detection means for detecting the thickness of said resist coating layer by using the ratio between reflected light of said third light beam from said resist master disc and said fourth light beam; and drive means for rotating said resist master disc and controlling the relative position between the first light beam irradiated on the surface of said resist master disc and said resist master disc in a radial direction of said resist master disc, said drive means controlling the speed of rotation of said resist master disc so that the linear velocity of said resist master disc at the position of irradiation of said first light beam is maintained at a constant value.

2. An apparatus as claimed in claim 1, further comprising a counter means for counting the number of faults detected by said fault detection means, and recording means for recording said number of faults counted by said counter means and said thickness of said resist coating layer detected by said thickness detection means, and wherein said drive means include radial position detection means for detecting a radial position of said resist master disc at which said first light beam is irradiated, and the radial position detected when a fault is detected by said fault detection means is also recorded in combination with said number of faults by said recording means.

3. A method of simultaneously detecting the characteristics of a resist master disc, comprising the steps of:

generating first and second parallel light beams from a single light source;

directing the first light beam to a first portion of the disc;

directing the second light beam to a second portion of the disc;

measuring the amount of light reflected from the first portion to develop a signal indicative of the presence or absence of faults on the surface of the disc while maintaining the linear velocity of the master disc constant in relation to the first beam; and simultaneously measuring the angle of reflection of the second beam from the second surface to develop a signal indicative of the thickness of the resist layer.

4. The method of claim 3 including the further step of simultaneously displaying the two signals.

* * * * *